US012773183B2

(12) United States Patent
Fedor

(10) Patent No.: US 12,773,183 B2

(45) Date of Patent: Oct. 27, 2026

(54) METHOD OF QUANTITATIVE ANALYSIS AND IMAGING OF THE ANTERIOR SEGMENT OF THE EYE

(71) Applicant: Peter Fedor, Traverse City, MI (US)

(72) Inventor: Peter Fedor, Traverse City, MI (US)

(73) Assignee: Peter Fedor, Traverse City, MI (US)

( * ) Notice: Subject to any disclaimer, the term of this patent is extended or adjusted under 35 U.S.C. 154(b) by 134 days.

(21) Appl. No.: 18/066,172

(22) Filed: Dec. 14, 2022

(65) Prior Publication Data

US 2023/0123560 A1 Apr. 20, 2023

Related U.S. Application Data

(62) Division of application No. 17/742,769, filed on May 12, 2022, now abandoned, which is a division of (Continued)

(51) Int. Cl.

*A61B 8/10* (2006.01)

*A61B 3/117* (2006.01)

(Continued)

(52) U.S. Cl.

CPC ................ *A61B 8/10* (2013.01); *A61B 3/117* (2013.01); *A61B 8/085* (2013.01); *A61F 2/16* (2013.01);

(Continued)

(58) Field of Classification Search

None

See application file for complete search history.

(56) References Cited

U.S. PATENT DOCUMENTS 5,487,388 A 1/1996 Rello et al.

5,551,432 A 9/1996 Iezzi (Continued)

FOREIGN PATENT DOCUMENTS

EP 2865324 A1 4/2015

OTHER PUBLICATIONS

Anterior segment changes during accommodation in eyes with a monofocal intraocular lens: High-frequency ultrasound study; Journal of Cataract Refract Surg; issue 34:pp. 949-956 (Year: 2008).*

(Continued)

*Primary Examiner* — Keith M Raymond

*Assistant Examiner* — Michael S Kellogg

(74) *Attorney, Agent, or Firm* — Aurora Consulting LLC

(57) ABSTRACT

What is provided are methods of analyzing at least one image of the anterior segment of an eye and for selecting an intraocular lens (IOL). The methods may include detecting at least one image from an anterior segment of the eye; identifying a location of a reference structure on the eye using a plurality of points of a landmark on the anterior segment of the eye; and calculating at least one quantitative dimension of the anterior segment of the eye using the reference structure. The newly identified landmarks and quantifiable dimensions improve the characterization of the anterior segment in order to better predict the position and movement of the intraocular lens. The improved methods for analyzing the imaging of the anterior segment of the eye allows for improvements in the refractive outcomes of cataract surgery, glaucoma procedures, refractive outcomes, and other eye-related diseases.

9 Claims, 5 Drawing Sheets

Related U.S. Application Data application No. 14/854,636, filed on Sep. 15, 2015, now Pat. No. 11,357,474.

(60) Provisional application No. 62/071,088, filed on Sep. 15, 2014.

(51) Int. Cl.

| | |
|---|---|
| ***A61B 8/08*** | (2006.01) |
| ***A61F 2/16*** | (2006.01) |
| *A61B 8/00* | (2006.01) |
| *A61B 34/10* | (2016.01) |
| *A61B 90/00* | (2016.01) |
| *A61F 9/007* | (2006.01) |

(52) U.S. Cl.

CPC ........... *A61B 8/4416* (2013.01); *A61B 8/5223* (2013.01); *A61B 2034/108* (2016.02); *A61B 2090/3735* (2016.02); *A61F 9/00736* (2013.01)

(56) References Cited

U.S. PATENT DOCUMENTS

| | | | | |
|---|---|---|---|---|
| 6,491,637 | B2 | 12/2002 | Foster et al. | |
| 6,887,203 | B2 | 5/2005 | Phillips et al. | |
| 8,608,314 | B2 | 12/2013 | Yoon et al. | |
| 8,687,866 | B2 | 4/2014 | Marziliano et al. | |
| 8,770,753 | B2 | 7/2014 | Hee et al. | |
| 8,967,810 | B1 | 3/2015 | Prager et al. | |
| 2004/0210139 | A1 * | 10/2004 | Coleman .................. | A61B 8/10 600/452 |
| 2012/0083667 | A1 | 4/2012 | Isogai et al. | |
| 2013/0258280 | A1 | 10/2013 | Goto | |
| 2014/0125949 | A1 * | 5/2014 | Shea .................... | A61B 3/1035 351/205 |
| 2014/0241605 | A1 | 8/2014 | Izatt et al. | |
| 2015/0092160 | A1 | 4/2015 | Chen et al. | |
| 2015/0150447 | A1 | 6/2015 | Huang et al. | |

OTHER PUBLICATIONS

Alward et al. “Anatomy of the Angle” Nov. 8, 2017; American Academy of Ophthalmology. Accessed Online at ; 6 pages (year 2017).

Borges-Giampani, et al. “Anatomy of Ciliary Body, Ciliary Processes, Anterior Chamber Angle and Collector Vessels.” Apr. 17, 2013; IntechOpen; DOI: 10.5772/52780; 25 pages (year 2013).

Howland, et al. “A standard nomenclature for the axes and planes of vertebrate eyes.” Vision Research 48 (2008): 1926-2917.

Li, et al. “Anterior segment optical coherence tomography and its clinical applications in glaucoma.” Journal of Current Glaucoma Practice, May-Aug. 2012; 6(2): 68-74 (year 2012).

Marchini, et al. “Anterior segment changes during accommodation in eyes with a monofocal intraocular lens: High-frequency ultrasound study.” J Cataract Refract Surg 2008; 34: 949-956 (year 2008).

Wang et al. “Exploring the Occurrence Mechanisms of Acute Primary Angle Closure by Comparative Analysis of Ultrasound Biomicroscopic Data of the Attack and Fellow Eyes” Pub. Biomed Research International vol. 2020, Article ID 8487907, 11 pages; accessed at (year 2020).

* cited by examiner

METHOD OF QUANTITATIVE ANALYSIS AND IMAGING OF THE ANTERIOR SEGMENT OF THE EYE

PRIORITY CLAIM

This patent application is a divisional of U.S. patent application Ser. No. 17/742,769, filed May 12, 2022; which is a divisional of U.S. patent application Ser. No. 14/854,636, filed Sep. 15, 2015; which claims priority to and the benefit of the filing date of provisional patent application U.S. Ser. No. 62/071,088, filed on Sep. 15, 2014, each of which is incorporated herein in its entirety.

FIELD

This patent application relates to imaging for use in measuring and analyzing dimensions and characteristics of the entire anterior segment of the eye.

BACKGROUND

Lens replacement surgery is replacing a natural lens, whether opaque from cataract or clear lens extraction, in an effort to reduce dependence on glasses. In lens-replacement surgery, the front capsule of the lens is opened and the lenticular material is permanently removed and replaced by the artificial intraocular lens (IOL). Usually the remnants of the anterior capsule and posterior capsule are left in place to provide support for the IOL. Cataract surgery is very common in elderly individuals with vision reduced by cataracts. Cataracts is a progressive clouding of the internal lens of the eye, preventing light from passing clearly through the lens and causing some loss of vision. Over an extended period of time, cataracts can cause blindness.

The introduction of the new generation of IOLs and the replacement of mild cataracts or natural lenses to correct the refractive errors of the eye has spurred the need for improved ways of predicting the exact position of the IOL and natural lens in patients for various procedures. There are difficulties with existing techniques for obtaining and identifying images of the eye suitable for quantitative analysis and for correctly calculating dimensions of the eye. Images that are tilted or are in paraxial locations often cause the measurements of the anterior segment of the eye to be altered and thus not suitable for quantitative analysis of the dimensions of the eye.

Several techniques exists for measuring and quantitatively analyzing the anterior segment of the eye. Ultrasound biomicroscopy (UBM) is one such technique used to image the anterior segment of the eye using high frequency ultrasound. For many years ultrasonic imaging with frequencies around 10 Megahertz (MHz) was mostly used in ophthalmology for imaging of the posterior segment of the eye. The posterior segment of the eye traditionally includes the retina and vitreous, while the anterior segment of the eye typically includes structures in the proximity of the cornea, iris, ciliary body, and the lens. After the introduction of high frequency ultrasound with frequencies around 30 to 60 Megahertz (MHz), UBM was adopted for more detailed evaluation of the anterior segment of the eye.

UBM has mainly been used for imaging and analyzing one isolated anterior angle of the eye for evaluation of glaucoma, instead of imaging and analyzing the entire anterior segment and the IOL. Traditionally, the anterior angle of the eye is the angle between the cornea and iris. The anterior chamber of the eye is the approximate space between cornea and iris, while the posterior chamber is the area between the iris and the lens. However, due to the limited depth of focus using UBM, several images are often required to be analyzed in parallel with one another to better analyze the anterior segment of the eye. The landmarks, parameters, and terminology that have been developed are mostly for the evaluation of only one anterior angle of the eye. Traditionally, single isolated scleral spur (SS) was used as a reference landmark for evaluation of only one anterior chamber angle. Some of the parameters commonly used for quantitative analysis of the single anterior angle include angle opening distance (AOD) and trabecular-iris space area (TISA). As a result of not analyzing the entire anterior segment of the eye, several parameters are missed and the information from the single image is not sufficient for quantitative analysis of the entire anterior segment.

Currently, several landmarks are clinically used to evaluate the anterior segment of the eye. The various landmarks include the anterior corneal vertex, the anterior lens vertex, the posterior lens vertex, the anterior angle recess, and the sulcus. Several distances, such as white-to-white distance (WTW), angle-to-angle distance (ATA), anterior chamber depth (ACD), pseudophakic anterior chamber depth (pACD), lens thickness (LT), sulcus to sulcus distance (STS), capsular bag diameter (CBD), and ciliary ring diameter (CRD), are commonly used to describe imaging of the anterior segment of the eye. Pavlin et al. suggested the use of scleral-iris angle (SIA) and scleral-ciliary process angle (SCPA) for evaluating the angle of the iris and the ciliary body of the eye. These angles use the external surface of the scleral spur as a reference plan and do not evaluate the relationship of the iris and the ciliary body with the lens or the IOL. In addition, several of the landmarks, such as the sulcus, the apex of the ciliary body, the external surface of the scleral spur, and scleral spur are difficult to identify on single frames of ultrasonic images.

Currently, axial length of the eye, white-to-white distance (WTW), anterior chamber depth (ACD), lens thickness (LT) are used to calculate the optimal power and select the optimal intraocular lens (IOL) to be implanted in the eye for the purpose of cataract or lens replacement surgery, where at least part of the natural lens is replaced. Cataract surgery is one of the most common surgeries in medicine, usually performed in elderly patients with hazy natural lens. On the contrary, the surgery of phakic intraocular lens implantation (also called implantable contact lens) is rare surgery designed to correct high refractive errors, such as myopia (nearsightedness). Phakic intraocular lenses (phakic IOLs) are implanted in front of the natural lens and no part of the natural lens is replaced. White-to-white distance (WTW) and Sulcus-to-sulcus distance (STS) are currently used to calculate the optimal power and select the optimal phakic intraocular lens.

Since many structures in the anterior segment of the eye move in response to various elements, such as light, pharmacological agents, and effects of cataract surgery, there is a need to recognize structures that do not significantly change their position in order to more accurately evaluate the movement of other structures in the eye. Thus, the identification of additional appropriate reference landmarks and parameters are necessary for accurately analyzing the anterior segment of the eye.

SUMMARY

What is provided are methods of analyzing at least one image of the anterior segment of an eye and for selecting an intraocular lens. The methods may include detecting at least one image from an anterior segment of the eye; identifying a location of a reference structure on the eye using a plurality of points of a landmark on the anterior segment of the eye; and calculating at least one quantitative dimension of the anterior segment of the eye using the reference structure. The reference structure may be a reference frontal plane, a reference anterior corneal surface, or a reference posterior corneal surface. In some embodiments, the methods may include determining a parameter corresponding to one or more of a ciliary body angulation and/or an iris angulation in relation to the reference frontal plane. The landmark on the anterior segment of the eye includes one or more of scleral spur, Schwalbe's line, ciliary body apex, peripheral iris pigment epithelium, anterior surface of the iris, and/or central iris pigment epithelium.

The newly identified landmarks and quantifiable parameters may be used to improve the characterization of the anterior segment in order to better predict the position and movement of the IOL and to better understand the mechanisms of eye diseases, such as glaucoma. In addition, the improved method for analyzing the imaging of the anterior segment of the eye allows for improvements in the refractive outcomes of cataract surgery and other clinical procedures, such as lens replacement surgery and the development of better accommodating IOLs.

The anterior angle of an eye in a 3-dimensional interpretation consists of an infinite number of radial 2-dimensional anterior angles of the eye that are 360 degrees around the center of the eye. The image of one isolated 2-dimensional anterior angle may contain many structures, such as cornea, Schwalbe's line, trabecular meshwork, scleral spur, and iris. If the 2-dimensional image of the anterior segment of the eye contains two contralateral anterior angles in one image, additional measurements can be obtained, that characterize not only the size of the anterior angle, but also the size of the whole anterior segment.

BRIEF DESCRIPTION OF THE DRAWINGS

Subject matter is particularly pointed out and distinctly claimed in the concluding portion of the specification. Claimed subject matter, however, as to structure, organization and method of operation, together with objects, features, and advantages thereof, may best be understood by reference to the following detailed description if read with the accompanying drawings in which:

DETAILED DESCRIPTION

In the following detailed description, numerous specific details are set forth in order to provide a thorough understanding of the examples as defined in the claimed subject matter, and as an example of how to make and use the examples described herein. However, it will be understood by those skilled in the art that claimed subject matter is not intended to be limited to such specific details, and may even be practiced without requiring such specific details. In other instances, well-known methods, procedures, and components have not been described in detail so as not to obscure the invention defined by the claimed subject matter.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

The description may use perspective-based descriptions such as up/down, back/front, and top/bottom. Such descriptions are merely used to facilitate the discussion and are not intended to restrict the application of embodiments of the present invention.

The term "contralateral" is used herein to describe the locations of the plurality of points of landmarks on the anterior segment of the eye and means on or related to the opposite side of the respective landmark from the first point.

In various embodiments, structure information of the anterior segment of the eye may be obtained using UBM and/or Optical Coherence Tomography (OCT) imaging and/or photography and/or other imaging methods. Such imaging may be two-dimensional (2-D) or three dimensional (3-D), depending on the application. Imaging and related aspects of the methods herein may be performed by a UBM and/or OCT imaging device coupled to, or integrated with, one or more computing devices.

Figure 1:
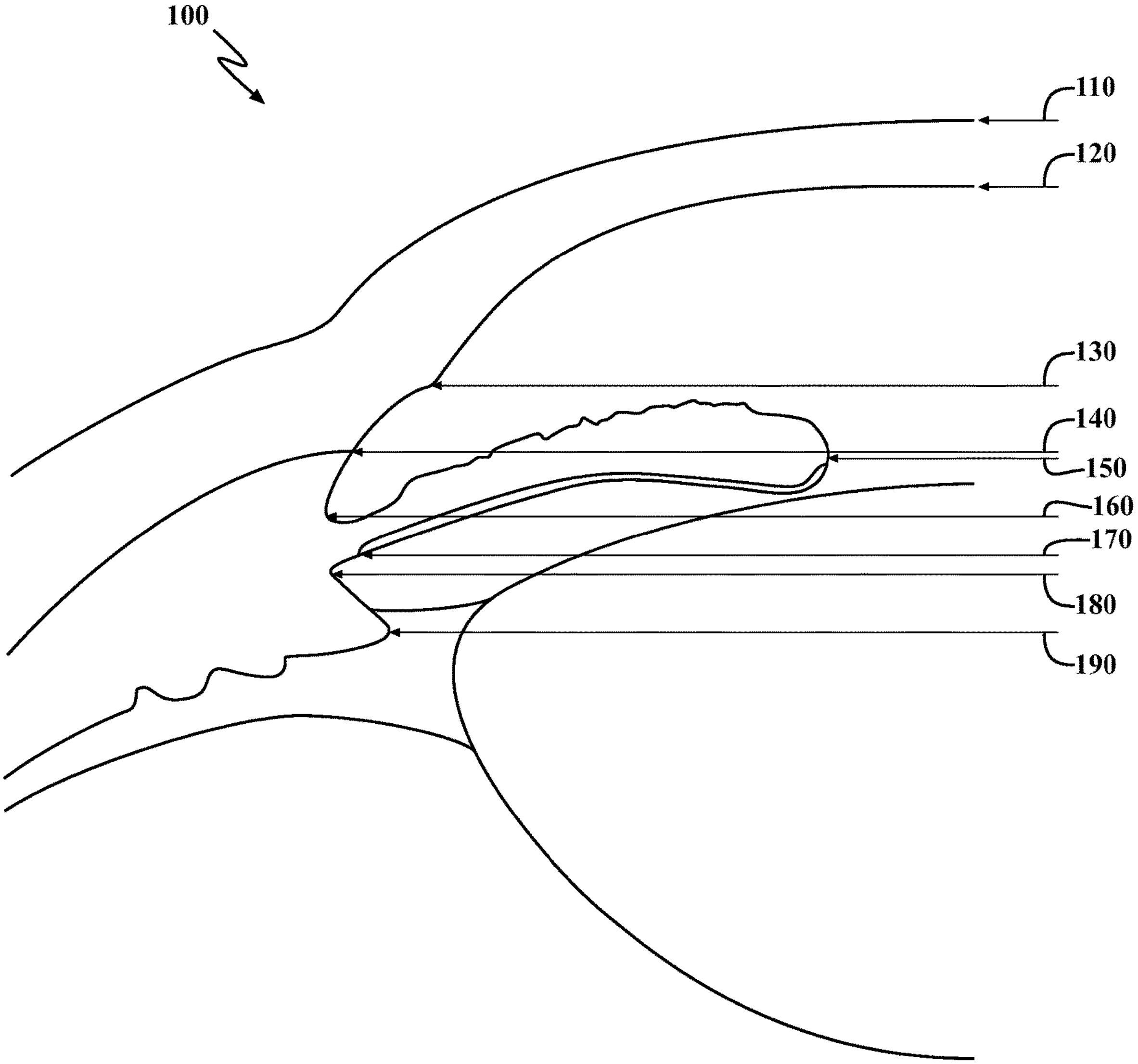
FIG. 1 shows the locations of reference structures and landmarks on the anterior segment of the eye.

Referring to FIG. 1, FIG. 1 shows the locations of reference structures and landmarks on the anterior segment of the eye that may be detected through an image 100. The anterior vertex of cornea (cornea) 110, the posterior vertex of cornea 120, Schwalbe's line 130, scleral spur 140, the central edge of the iris pigment epithelium (IPE) 150, the anterior angle recess 160, the peripheral edge of IPE 170, the ciliary sulcus 180, the apex of the ciliary body 190 are all shown in FIG. 1. The landmarks may include one or more of scleral spur, Schwalbe's line, ciliary body apex, peripheral iris pigment epithelium, central iris pigment epithelium, and/or any other landmarks derived from these landmarks. In some embodiments, the landmarks have at least two points that are located in a contralateral position from each other.

Since it is not possible to analyze the depth or width of any structures or to calculate the quantitative dimensions of the anterior segment of the eye based solely on one point of a landmark, at least two points of a landmark must be analyzed. By using a plurality of points of a landmark, a location of a reference structure may be identified. In some embodiments, two points of a landmark may define a reference frontal line, while three points of a landmark may define a reference frontal plane. For example, two approximately contralateral landmarks of scleral spur may be used to analyze the size of the anterior segment of the eye. In some embodiments, the anterior corneal surface of the eye and the posterior corneal surface of the eye may be both used as references for calculating quantitative dimensions of the anterior segment after UBM imaging since these structures do not substantially change and are easily recognized and detected. In order to quantitatively analyze and measure the anterior segment of the eye, it is not necessary to obtain images from the whole volume of the anterior segment since the most relevant images are located around the central axis. The location of the reference frontal plane may be imaged and measured from one or more of a horizontal direction, a vertical direction, a direction of shortest measurement, a direction of longest measurement, a first ciliary apex to a second ciliary apex, a first scleral spur to a second scleral spur, and/or a first peripheral iris pigment epithelium to a second peripheral iris pigment epithelium. The reference structures allow for comparing the images after physiological changes or medical interventions have occurred. These reference structures also allow for the identification of the position of other landmarks.

In some embodiments, the final image used for quantitative analysis includes the whole anterior segment. The final image used for quantitative analysis may be chosen automatically as the image with the largest pupillary diameter. In other embodiments of imaging the anterior segment of the eye, several images close to the pupillary axis may be obtained. For example, this may include an area of 1-3 mm.

Figure 2:
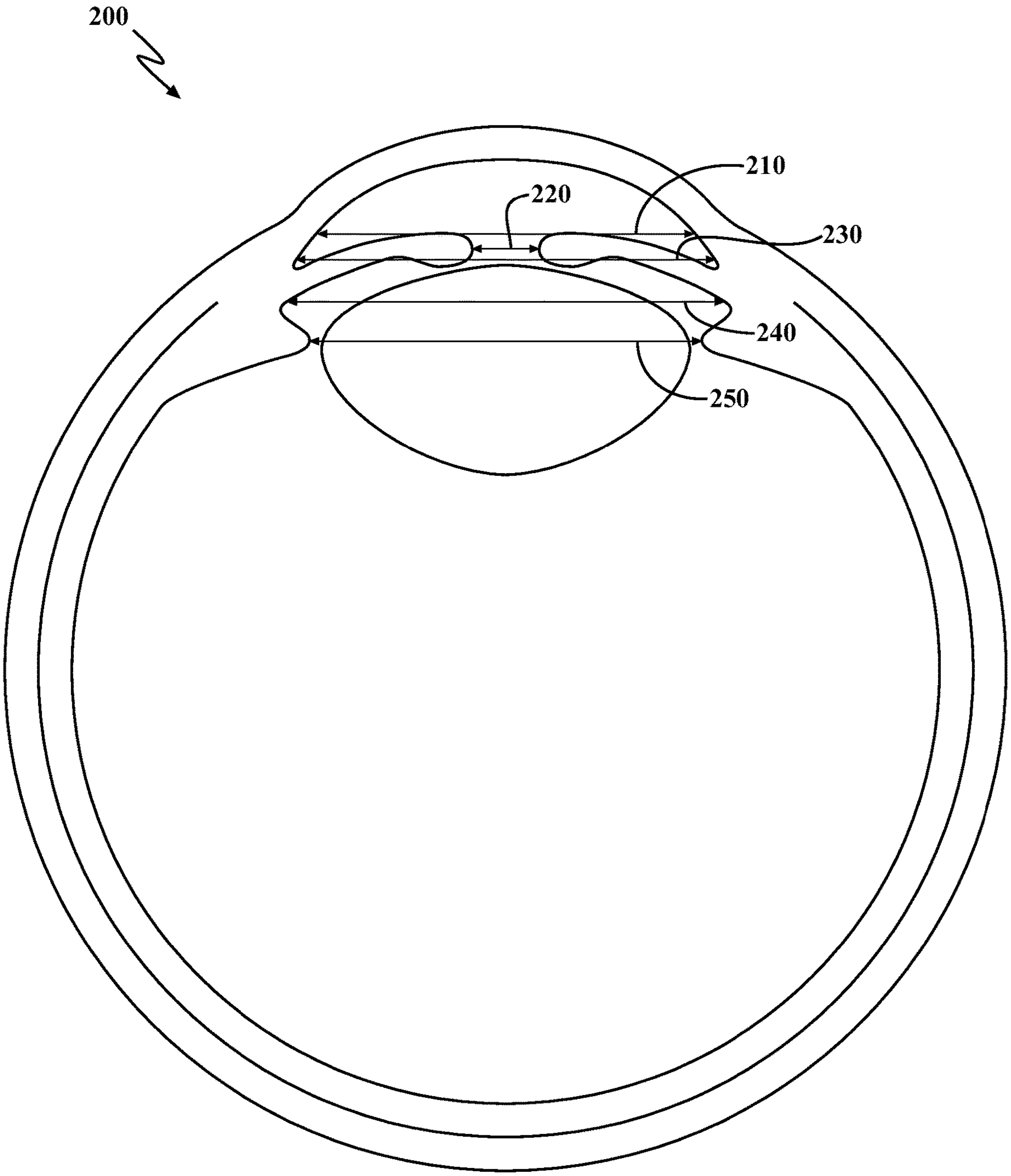
FIG. 2 shows the distances in the reference frontal plane of the anterior segment of the eye to be used as parameters for the anterior segment of the eye.

The most common currently used measurements of the anterior segment are: (1) White-to-White distance (WTW), which is the distance between the corneal limbuses (between the edges of sclera of the white part of the eye); (2) Angle-to-angle distance (ATA), which is the distance between the anterior angle recesses; (3) Sulcus-to-sulcus distance (STS), which is the distance between both sulcus recesses; (4) Ciliary ring diameter (CRD), which is the distance between both apices of ciliary body; and (5) Anterior chamber depth (ACD), which is the distance between the anterior vertex of lens and cornea. Referring to FIG. 2, FIG. 2 shows distances in the reference frontal plane of the anterior segment of the eye to be used as landmarks for the anterior segment of the eye 200. Specifically, Schwalbe's line to Schwalbe's line distance 210 is the distance between both Schwalbe's lines typically imaged on one scan of the anterior segment. The margin-to-margin distance 220 is the central iris pigment epithelium to central iris pigment epithelium distance, which is the distance between both pupil margins. The spur-spur distance 230 is the distance between both scleral spurs. The peripheral IPE to peripheral IPE distance 240 is the distance between both points on the peripheral edge of the iris pigment epithelium. The apex of ciliary body to apex of ciliary body distance is shown as 250. The apex of the ciliary body is a well-known anatomical structure in the field that includes the centripetal tip/end of the ciliary body. The distances shown in FIG. 2 are the largest distances between respective antipodal points (chords) and are measured on the images passing through the center of the eye. The distances through the center of spherical or elliptical structures are also referred to as diameters.

As used herein, the term "axial direction" means the axial direction of the eye and is consistent with the optical, geometrical, pupillary, or other axis of the eye. This is in a different direction than the axis of the head and human body, as the axis of the eye is perpendicular to the axis of the human body.

As used herein, the term "frontal plane" means the frontal plane of the eye with the direction that is commonly understood by one of ordinary skill in the art which the disclosure belongs. In some embodiments, the frontal plane of the eye may be identified at the level of different landmarks of the eye. For example, the frontal plane at the level of the scleral spur is parallel, which means that the frontal plane is in a similar direction as a frontal plane at the level of apex of the ciliary body. In a two dimensional image, a frontal plane refers to the frontal line in the image that is part of the frontal plane. Other examples of body planes that are used in similar ways in the eye include a sagittal plane and a transverse plane that are perpendicular to the frontal plane in vertical and horizontal directions, respectively.

In one embodiment, the analysis of the video imaging of the anterior segment may start with review of several image frames, identification of at least one best image including the cornea and both contralateral anterior angles and areas of ciliary body, identifying the frontal plane of the eye at the level of contralateral scleral spurs or pupillary margins, drawing perpendicular line to frontal plane passing through anterior corneal vertex, measuring the distance between contralateral scleral spurs and measuring the distance between the spur-to-spur line and anterior corneal vertex, called scleral spur depth.

Due to the multiple and confusing terms and shortcuts currently used in anterior segment imaging, the following methodology is used herein:

The last letter of the multiple letter shortcut (such as ACD—anterior chamber depth) is generally defining the category of the term, where D is the depth, A is the angle, X is the axis, S is the segment, C is the chamber, Com is the compartment, Sp is the space, P is the pressure, G is the gradient, M is the membrane, V is the vault.

Points are described by single letters, where C is the cornea—anterior corneal vertex, I is the IPE—peripheral edge of iris pigment epithelium, M is the margin—pupil margin—defined as edge of central iris pigment epithelium, A is the angle—point of anterior chamber angle recess, X is the apex—cumulative apex of the ciliary body, S is the sulcus—ciliary sulcus recess, L is the line—Schwalbe's line (the anatomical structure of Schwalbe's line in single frame of the image is a point and not line), R is the spur—scleral spur, iO is the IOL optic—most anterior peripheral point of optic of IOL, iH is the IOL haptic—most anterior peripheral point of haptic of IOL, iA is the IOL—anterior IOL vertex—the anterior edge of the center of the IOL. In one embodiment, the cumulative apex of the ciliary body means that the apex is defined based on more than one image.

Horizontal and vertical distances in the frontal plane, such as currently used STS sulcus-to-sulcus distance, are generally connecting two reciprocal contralateral points on a two-dimensional image and are labeled as letter-to-letter. In general, YTY (Y-to-Y) is distance between two landmarks Y in frontal plane in horizontal direction (more specifically defined hYTY is horizontal YTY). Vertical YTY (vYTY) is in vertical direction (sagittal plane). In some embodiments, the axial distances are measured from anterior corneal vertex. Examples of the axial distances include ACD for anterior chamber depth and LD for Schwalbe's line depth.

In some embodiments, the following distances in the frontal plane provide benefits for describing the position of the structures of the anterior segment of the eye:

WTW: White-to-white distance is the distance between the peripheral white area of corneal limbus.

ATA: Angle-to-angle distance, Anterior angle-to-anterior angle distance is a distance between anterior chamber angle recesses.

LTL: The Schwalbe's line-to-Schwalbe's line distance is the distance between both Schwalbe's lines typically imaged on one scan of the anterior segment.

RTR: Spur-to-spur distance is the distance between both scleral spurs.

MTM: Margin-to-margin distance, the central iris pigment epithelium-to-central iris pigment epithelium distance is the distance between both pupil margins (M), typically imaged on one scan of the anterior segment. It is generally close to the pupil diameter.

ITI: IPE-to IPE distance, the peripheral iris pigment epithelium-to-peripheral iris pigment epithelium distance is the distance between both points I, typically imaged on one scan of the anterior segment.

XTX: Apex-to-apex distance, the cumulative apex of ciliary body-to-apex of ciliary body distance is the distance between both apices of CB typically compiled from images on multiple scans of the anterior segment.

The corresponding distances in the axial direction are as follows:

LD: The Schwalbe's line depth is the distance between anterior vertex of the cornea and LTL line.

RD: Scleral spur depth is the distance between anterior vertex of the cornea and RTR line.

MD: The margin depth is the distance between anterior vertex of the cornea and MTM line.

ID: The IPE depth is the distance between anterior vertex of the cornea and ITI line.

XD: The apex depth or apex of ciliary body depth is the distance between anterior vertex of the cornea and XTX line.

SD: Sulcus depth is the distance between anterior vertex of the cornea and STS line.

AD: Aqueous depth is the distance between posterior corneal vertex and anterior lens vertex. This equals to ACD minus corneal thickness.

As described herein, each angle has one vertex and two sides. The Frontal line (FL) is the reference line for described angles. In contrast to previously suggested definitions of angles in relation to an external scleral surface, the frontal line provides benefits by relating the structures of the eye to the position of the IOL, which is normally in the frontal plane. In some embodiments, the angle of the iris and/or ciliary body is in relation to reference frontal plane.

In some embodiments, there are several angles that are useful in describing the position of the structures of the anterior segment of the eye in relation to the lens/intraocular lens.

IA: Iris angle is the angle with the vertex in point I with two sides of frontal line (FL) and IPE line. IPE line is connecting peripheral and central IPE, that is points I and M. IPE distance is the distance between two edges of IPE, point I and point M.

CA: Ciliary body angle is the angle with two sides of the frontal line (FL) and the ciliary body axis (CX). The ciliary body axis (CX) is the line passing through the apex of the ciliary body and through the middle of segments between the anterior and posterior edges of ciliary body with equal distance to the apex (or alternatively in the direction perpendicular to FP). The vertex of CA is theoretically at the base of the CB, but this point is difficult to identify on ultrasound image. In a specific UBM scan it is easiest to measure it indirectly by placing the caliper in point X and extending the first side towards the opposite point X and the second side along the ciliary body axis and subtract the value of this measured angle from 180 degrees.

IPE vault (IV) is the largest distance perpendicular to IPE line between IPE line and posterior edge of the IPE.

In some embodiments, the IA may be a positive number if the iris is angled anteriorly compared to frontal plane at the level of peripheral IPE-to-peripheral IPE line, or negative number if iris is angled posteriorly. Similarly CA may be positive or negative as compared to the frontal plane. In many eyes the IA and CA have the same direction and sign. In some eyes the IA and CA can have different direction and sign. In many eyes with cataract and relative pupillary block, angle IA is positive reflecting the anterior shift and bowing of iris, but angle CA is close to zero reflecting no significant forces acting on IOL.

For example, in pesudophakic eyes, the iris is typically close to the frontal plane. Angles IA is close to zero, reflecting that no anterior or posterior force is acting on iris in axial direction. In another example, in eyes with cataract and sometimes in pseudophakic eyes, the angle IA is often positive between 1 to 15 degrees, with the iris angled anteriorly, reflecting the amount of pressure gradient directed anteriorly or the displacement by the anterior growth of the lens. In yet another examples, in eyes with pigment dispersion syndrome, the IA is often negative, reflecting posterior bowing of the iris.

The ciliary angle (CA) may be positive or negative. This could be caused by the mechanical displacement of structures such as a result of anterior growth of the lens or by forces originating in the posterior segment. The posterior force may reflect several factors, such as increased volume of vitreous, space occupation by posterior growth of the lens or accumulation of fluid in the posterior segment. The amount of this angle is intuitively related to the amount of these forces.

There are several points, distances and angles that are useful in describing the position of the IOL and structures of the anterior segment of the eye.

iA: Anterior vertex of the IOL (iA) is the point on the anterior surface of the IOL in the center of the optic of the IOL. This is the point describing generally the position of the IOL within the eye. In some embodiments, the IOL is well centered in frontal plane with no tilt. The IOL can be sometimes tilted or displaced to the side, or show anterior or posterior bowing, or move in the eye during accommodative effort, which is described later in the text. Some IOLs are single-piece and some are three-piece IOLs, with one central optic and two peripheral haptics. Each of these parts can have different tilts.

iO: IOL optic—Peripheral anterior edge of the IOL optic (iO) is the most peripheral and anterior point of the part of IOL used for optical purposes.

iH: IOL haptic—Peripheral and anterior edge of IOL haptic (iH) is the most peripheral and anterior point of the haptic or in the absence of haptic the most peripheral and anterior point of IOL.

The depth of IOL is the axial position of the IOL in relation to anterior corneal vertex. Depth of IOL is described for several parts of IOL: iAD, iOD, iHD.

iACD: IOL depth or IOL anterior chamber depth is the distance from iA to C. This is also called pseudophakic ACD and is the main descriptor of the axial IOL position within the eye. Alternatively, IOL aqueous depth (IAD) is defined as the distance of posterior corneal vertex to iA.

In some embodiments, the IOL position is at the level of CB. The relative depth of IOL is the axial position of the IOL in relation to apex-to-apex distance (XTX), that corresponds to the position of the apex of ciliary body is usually close to zero. This is in contrast to pseudophakic ACD, which is the distance between anterior vertex of cornea and anterior vertex of IOL. Relative depth of IOL is described for several parts of IOL: iACD, iOD, iHD.

iAR: IOL relative depth is the perpendicular distance from iA to XTX. It may be positive (anterior) or negative (posterior) number, but it is usually close to zero. The position of the haptic (represented by iH point) may be in the ciliary plane (neutral), retrociliary (posterior) or rarely anterior to the apex of CB.

The Effective lens position (ELP) is not the same as IOL depth (iAD). ELP is a theoretical distance derived from the concept of thin-lens optics used in traditional IOL power calculation formulas. In some embodiments, ELP is the distance from corneal vertex to the plane where the power of the IOL acts in the theoretical vergence formula, which is the approximation of the thin-lens concept. The thin-lens optics ignores the thickness of the IOL. The ELP plane is somewhere between the anterior and posterior vertex of the IOL and it is not easy to calculate it as the exact geometrical designs of each IOL style and power of IOL are frequently confidential.

In some embodiments, the iris lens (IL) distance (same direction as depth) is the shortest distance between the central edge of iris (M) and anterior surface of IOL in perpendicular direction to frontal plane. The iris lens (IL) touch is the situation when any part of anterior surface of IOL optic is in touch with any part of IPE. The IL touch is related to applications related to pigment release and pigmentary glaucoma.

In some embodiments, the haptic-to-apex (HTX) distance is close to zero, as the haptic often touches the apex of the IOL. It may be positive number, when there is a space between the end of haptic and apex of CB, or a negative number, when there is a overlap of end of haptic and apex of CB. The haptic-to-haptic (HTH) distance is the distance between iH and iH. This can change inside of the eye with flexible haptics. In some embodiments, the IOL plane is the plane defined by the anterior edge of the IOL optic (points iO). For clinical applications, the IOL tilt angle is the angle between IOL plane and frontal plane with the vertex in point iO.

OL by the ciliary body, there is usually not anterior or posterior bowing of IOL.

According to one embodiment, the method of analyzing at least one image of the anterior segment of an eye comprises detecting the at least one image of the anterior segment; identifying a location of a reference frontal plane of the eye using a plurality of points of a landmark on the anterior segment of the eye; determining a parameter corresponding to one or more of a ciliary body angulation and/or an iris angulation in the reference frontal plane; and calculating at least one quantitative dimension of the anterior segment of the eye using the ciliary body angulation and/or an iris angulation. The ciliary body angulation is a ciliary angle located between the reference frontal plane of the eye and a line corresponding to at least two connected points located between an anterior ciliary body edge and a posterior ciliary body edge in an axial orientation.

Figure 3:
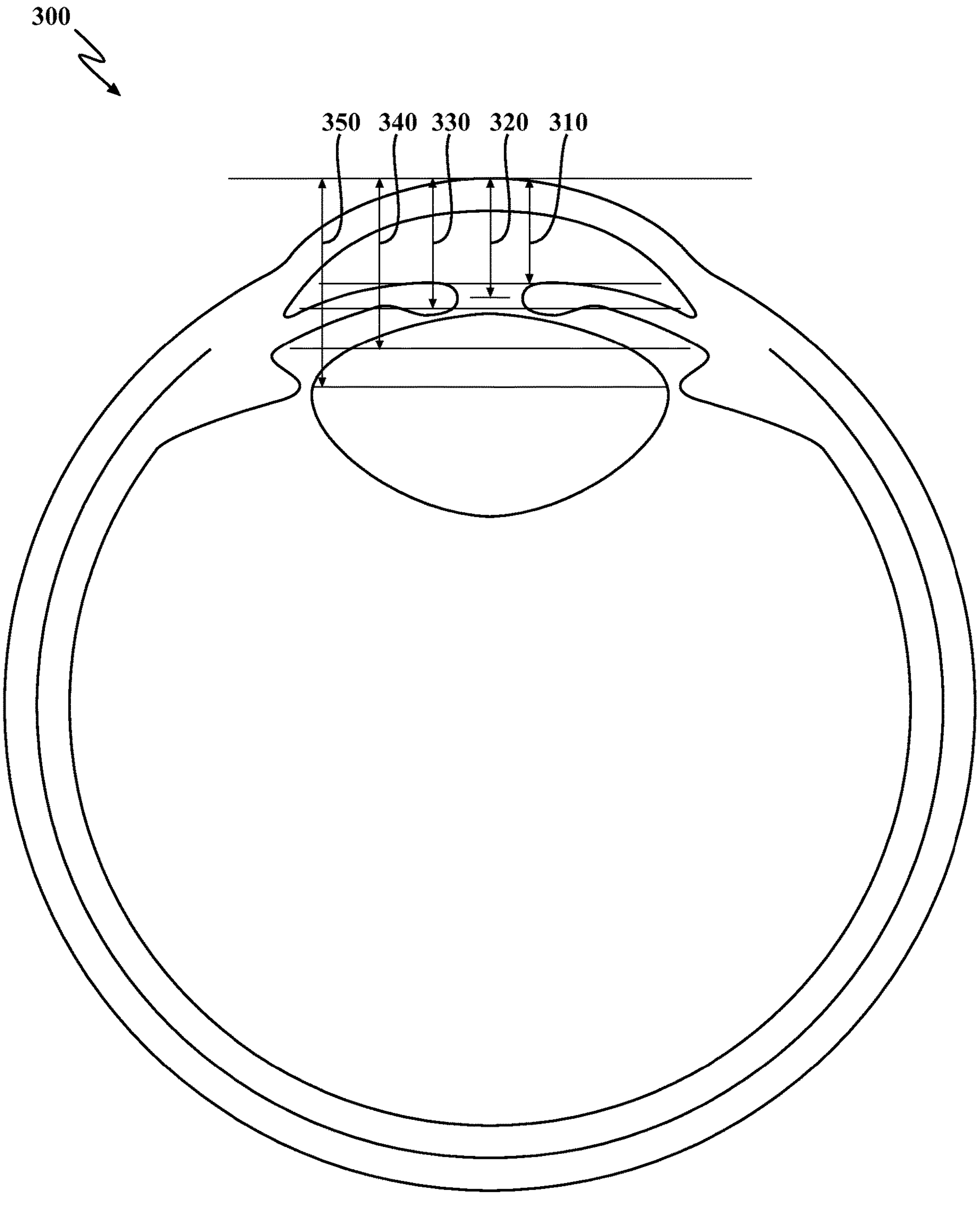
FIG. 3 shows the distances in the axial direction to be used as parameters for the imaging of the anterior segment of the eye.

Referring to FIG. 3, FIG. 3 shows the distances in the axial direction to be used as parameters for the imaging of the anterior segment of the eye 300. FIG. 3 shows various depth distances including LD 310, MD 320, RD 330, ID 340, and XD 350.

Figure 4:
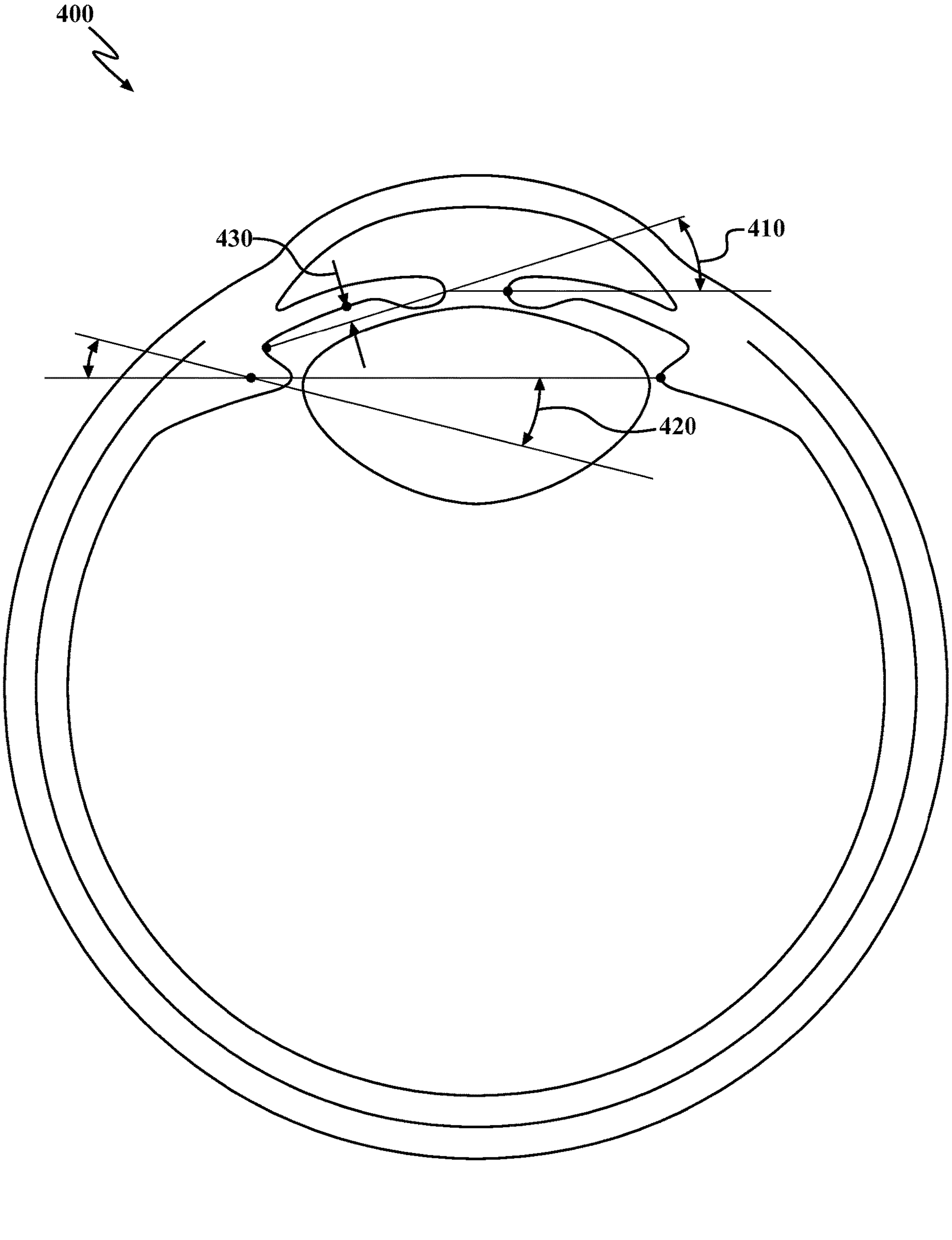
FIG. 4 shows the angles related to the position of IOL to be used as landmarks on the anterior segment of the eye.

Referring to FIG. 4, FIG. 4 shows the angles related to the position of IOL to be used as landmarks on the anterior segment of the eye 400. FIG. 4 shows an Iris angle (IA) 410, a ciliary/ciliary body angle (CA) 420, and an iris vault (IV) 430.

Landmarks that are relatively easy to define in a reproducible manner include contralateral points of scleral spur, the iris pigment epithelium (IPE), cornea and apices of ciliary body as opposed to previously used angle-to-angle and sulcus-to-sulcus measurements. In one embodiment, a method of analyzing at least two images of the anterior segment of an eye comprises detecting the at least two images and identifying a location from a plurality of locations corresponding to a position of the ciliary body in the eye. The position of the ciliary body may be an apex and the apex is identified by superimposing a first image onto a second image. In other embodiments, several images in peri-pupillary area are superimposed to allow better definition of the ciliary body. The reconstruction of a final image used for quantitative analysis may include overlay of several images. The superimposing may occur in space or in time.

The iris pigment epithelium (IPE) has strong signal on ultrasonic image with relatively distinct edges, which is important for reproducible identification of landmarks. The central edge of iris pigment epithelium, also called pupillary margin (M) is defined as the most central point of strong signal of IPE and peripheral edge of iris pigment epithelium (I) is defined as the most anterior and peripheral point of strong signal of IPE.

Scleral spur (R) has relatively strong signal and is relatively easily defined on most scans as an area of change of curvature and has characteristic shape. As part of our invention it is recognized that preferred reference plane can be defined by two contralateral points of R on a single scan, or any 3 points of R in three dimensional space can define a reference plane. These landmarks do not significantly change its position and are easily defined. Alternatively point I can be used as well.

The anterior corneal curvature (ACC) and posterior corneal curvature (PCC) could serve each as a reference landmark, as they do not change significantly.

The point of Schwalbe's line (L) is recognized by ultrasonic image and is defined as the point of change of curvature of the convex shape on the inner edge of corneal endothelium.

In some embodiments, the reference line in the frontal plane (FP) is used for definition of angles of different structures (for example frontal-ciliary angle) rather than the previously used tangent to scleral surface for the purpose of analyzing the lens position, instead of the anterior angle for glaucoma. The frontal plane (FP) and its corresponding line in two-dimensional images called frontal line (FL) are also important for consistent measurements of any distances in axial direction (sagittal or transverse planes) as these are all measured perpendicular to FP and FL. The frontal plane (FP) and line (FL) of the anterior segment (AS) of the eye can be defined by several lines or a combinations of them.

In one embodiment, the line connecting contralateral scleral spurs, contralateral central IPE (M) or contralateral peripheral iris pigment epithelium (I) is used to define FP. Alternatively it is recognized that the line defined by sulcus-to-sulcus distance (STS) or white-to-white (WTW), or the line connecting both Schwalbe's lines (L) or a combination of any of previous landmarks can all be used to define frontal plane of AS.

In one embodiment, the anterior corneal vertex point (aC) may be defined as the most anterior point as compared to the frontal plane of the anterior segment (FP). The anterior chamber depth (ACD) may be defined as the distance of aC to the lens in a plane perpendicular to FP. Similarly, for example, the spur depth (RD), IPE depth (ID), margin depth (MD) and apex depth (XD) can be defined as the distance of aC to the appropriate landmark in a plane perpendicular to FP. These distances can be used meaningfully in clinical practice.

Figure 5:
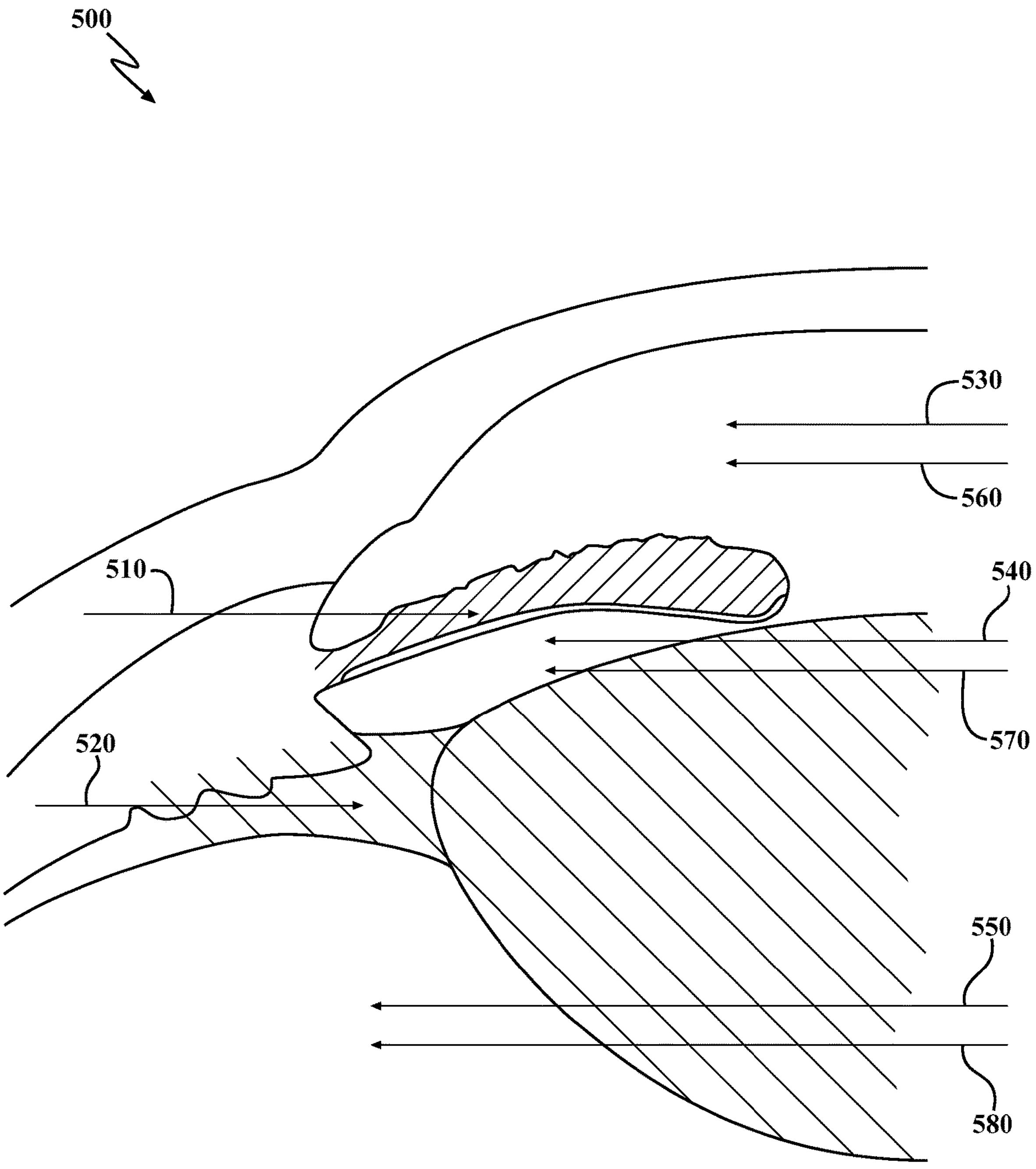
FIG. 5 shows the locations of compartments, membranes and pressures related to the position of the IOL on the anterior segment of the eye.

Instead of using only one intraocular pressure (IOP) and three chambers (AC: Anterior chamber, PC: Posterior chamber, and VC: Vitreal cavity), the embodiments disclosed herein involve the use several characteristics to better describe the position of the artificial lens and the natural lens. There are several spaces and pressures that have been identified to be useful in describing the position and movement of the IOL and the structures of the anterior segment of the eye. Referring to FIG. 5, FIG. 5 shows the locations of compartments, membranes and pressures related to the position of the IOL on the anterior segment of the eye 500. In relation to the iris member 510 and the ciliary membrane 520, FIG. 5 shows the anterior compartment or space (ACom) 530, the intermediate compartment or space (ICom) 540, and the posterior compartment or space (PCom) 550. In addition, FIG. 5 depicts the location of the anterior intraocular pressure (AIP) 560 on the ACom 530, the intermediate intraocular pressure (IIP) 570 on the intermediate compartment 540, and the vitreal (posterior) intraocular pressure (VIP) 580 on the PCom 550.

In some embodiments, the intralenticular space and choroidal space may have also have independent eye pressures. The Vitreo-Anterior gradient (VAG) or Postero-anterior gradient (PAG) is the pressure gradient between VIP and AIP and is calculated as VIP minus AIP. The IV is the result and reflects intermediate-anterior intraocular pressure gradient between IIP and AIP.

Since the iris and lens/IOL-zonules-ciliary body complex may act as separate biochemical barriers, the ciliary membrane (CM) is identified in a separate location from the iris membrane (IM). As a result, the IM is defined by the iris, which may or may not be in contact with the capsule of the lens. In eyes with cataract, the iris is frequently convex reflecting higher pressure in ICom as compared to ACom (positive I/A pressure gradient). The iris vault changes depending on the pressure gradient between ICom and ACom. The IM may also be concave with negative iris vault values, as for example in Pigment Dispersion Syndrome. In most pseudophakic eyes, the IM is frequently in neutral position In some embodiments, the ciliary membrane (CM) is defined by the complex of lens-IOL-zonules-ciliary processes-ciliary body. It is recognized that CM is mechanical barrier as well as sometimes is semipermeable to particles or fluids and can cause obstruction of flow and pressure gradient between posterior and intermediate compartments. The ciliary membrane depending on if a lens or intraocular lens constitutes part of the membrane can be referred to as ciliary-lens membrane (CLM) or ciliary-IOL membrane (CIM). Since the position of the lens is dependent on the movement of the ciliary membrane, the ciliary membrane can move independently from the iris membrane. The obvious example is the significant movement of the iris membrane after peripheral iridotomy in relative pupillary block and no or minimal movement of the ciliary membrane and lens. In some embodiments, it is possible that small movements of lens are often not accompanied by respective movements of iris.

In order to improve the refractive outcomes of cataract surgery and to develop better IOLs allowing focused vision at a distance and near without glasses, a more detailed analysis of the position and movement of the lens/IOL is needed. The lens/IOL is in the capsular bag and is directly attached to the ciliary body through the zonules. This complex ciliary membrane and its movement directly changes the lens or IOL position. Some other structures can exert force and move this membrane either mechanically directly (such as for example movement of ciliary muscle during accommodation or after cataract surgery), or through the action of pressure of fluid (such as aqueous misdirection syndrome). The iris can also exert force on ciliary membrane either through aqueous fluid or almost directly with an area of iris-lens touch.

The main benefits from using two separate biomechanical boundaries are simpler description and analysis of the position and movement of IOL. This can be used for better IOL power prediction and development of IOL allowing pseudo-accommodation. The ciliary membrane reflects the position and movement, allowing for easier analysis of mechanical factors that influence it, such as capsulorhexis and the position of the haptics of IOL. In addition, it becomes easier to identify the biomechanical forces observed from fields of glaucoma, myopia, hyperopia, and the development of the eye.

The central axis of the eye could be pupillary axis, optical axis or other suitable axis of the eye. The pupil is frequently displaced medially to the geometrical axis of the eye. The pupillary axis is relatively closer to optical axis of the eye as compared to geometrical axis in most eyes. The pupil also changes with light, fixation at distant or near objects (accommodation), pharmacological agents and other factors.

The measurements in the frontal plane of the eye, such as sulsus-to-sulcus dimension (STS) or white-to-white corneal measurement (WTW) are called frontal measurements. Frontal measurements are altered by paraxial location and are not significantly altered by tilt. They require the use of image close to the central axis at the level of the measured landmark.

In one embodiment, the final measurement used for quantitative analysis is chosen automatically from the image with the largest diameter between both sides of the measured landmark. Examples include RTR, ITI, MTM, LTL, ATA or pupillary diameter. The measurements in sagittal or axial planes of the eye, such as ciliary body depth (CBD), where CB may not be well defined in single scan may require information from multiple scans. The center of the pupil may then be defined as the image with largest pupil diameter or superposition of images close to the largest pupillary diameter. The measurements in sagittal or axial planes of the eye, such as anterior chamber depth (ACD) are altered by the tilt as well as paraxial location. In some embodiments, the tilted and paraxial measurements may be similar to perpendicular axial measurements.

To obtain a desired refractive outcome of an IOL implantation, different methods of intraocular lens power calculation are used. All major formulas currently use the measured axial length of the eye and the measured keratometric corneal power and estimate the postoperative position of the IOL. Most of the formulas use a constant that depends on the IOL model to estimate the position of the IOL in the eye. The name of this constant differs in different IOL power calculation formulas, such as A-constant or Surgeon factor.

Other new generation formulas use complex mathematical and optical methods to estimate the position of the IOL in the eye, but the general problem of better estimate of the exact axial and three-dimensional position of the IOL remains. The exact position of the IOL in the eye appears to be at present the major source of error predicted refractive outcome. No method currently recognizes the role of anterior segment imaging for individual sizing of the diameter of IOL in lens replacement surgery. Lens replacement surgery is replacing a natural lens, whether opaque from cataract, or clear lens extraction in an effort to reduce dependence on glasses. In lens-replacement surgery the front capsule of the lens is opened and the lenticular material is permanently removed and replaced by artificial intraocular lens. Usually the remnants of the anterior capsule and posterior capsule are left in place to provide support for the IOL.

With the introduction of new generation of IOL's and replacement of mild cataracts or natural lenses to correct the refractive errors of the eye and decrease dependence on glasses new issues are critically important. It is recognized, that there is need for improved precision of prediction of exact position of the intraocular lens so that patients see well at distance without glasses. In some embodiments, accommodating IOL (A-IOL) may improve focusing of the eye after lens replacement surgery using different methods. One of these methods is movement of the IOL, whether movement of the whole IOL structure or the movement of its edges by changing of its shape. It is recognized, that there is need for improved precision of prediction of exact position of the intraocular lens, its movement and change of the IOL shape so that patients see well at distance and near without glasses.

The horizontal dimensions of the IOL and its relation to the anatomical structures of the eye are important in achieving certain refractive outcome. However, the horizontal dimension of the IOL, such as sizing of the diameter of the IOL, is not used in lens replacement surgery. In some embodiments, the IOL is selected by a method comprising detecting at least one image from the anterior segment of the eye; identifying a location of a reference frontal plane of the eye using a plurality of points of a landmark on the anterior segment of the eye; determining at least one parameter based on at least one measurement of the reference frontal plane; and selecting at least one characteristic of the intraocular lens to be implanted into the eye using the at least one parameter. The intraocular lens may be implanted into an eye to postoperatively render the eye with any chosen refractive outcome at distance and at near fixation. This method may be applicable to intraocular lenses or other implanted substances placed in the proximity of remnants of an anterior capsule as for example in the capsular bag or ciliary sulcus. The selection of IOL to be implanted into an eye to achieve desired refractive outcome is based on the knowledge of exact position and movement of an intraocular lens in the eye after the surgery.

The improved accuracy of the prediction of refractive outcome with specific IOL is attained by considering the effect of each individual's individual size and shape of the IOL for the individual anatomy of a particular patient, on the position of the IOL in all three dimensions (as for example axial location, tilt, rotational position of an IOL) and on the movement of the intraocular lens or change of its shape in the eye. Exact three dimensional position of IOL's and its movement thus become crucial for the success of correction of optical aberrations and accommodation. This requires improvements in the methods of selection of IOL to be implanted in a specific eye. The exact position of the IOL is not determined only by the characteristics of the IOL and anatomy of natural eye, but also on the anatomical changes caused by the surgery.

It will, of course, be understood that, although particular embodiments have just been described, the claimed subject matter is not limited in scope to a particular embodiment or implementation. Likewise, an embodiment may be implemented in any combination of compositions of matter, apparatuses, methods or products made by a process, for example. The subject matter of the present disclosure includes all novel and non-obvious combinations and subcombinations of the various elements, features, functions and/or properties disclosed herein.

The invention claimed is:

1. A method for selecting an intraocular lens for an eye, comprising:

receiving at least one image of a cross-section of an anterior segment of the eye;

identifying a location of a reference frontal plane on the anterior segment of the eye, wherein the reference frontal plane comprises a line on the at least one image connecting at least two contralateral landmarks of a same type;

determining at least two different parameters in relation to the reference frontal plane, wherein the at least two different parameters are selected from the group consisting of: a scleral spur depth, a lens thickness, and an iris angulation;

identifying at least one characteristic of the intraocular lens to be implanted into the eye during an eye surgery, based on the at least two different parameters; and applying a selection of the intraocular lens to implantation in the eye, based on the identified at least one characteristic of the intraocular lens.

2. The method of claim 1, wherein the at least one characteristic of the intraocular lens is a power of the intraocular lens.

3. The method of claim 1, wherein the at least one characteristic of the intraocular lens is a diameter of the intraocular lens.

4. The method of claim 1, wherein a parameter of the at least two different parameters comprises the iris angulation, wherein the iris angulation is represented by a first side of an angle being the reference frontal plane and a second side of the angle being a line or a curve representing a posterior surface of the iris.

5. The method of claim 1, wherein the at least two contralateral landmarks of the same type comprise two points of a scleral spur.

6. The method of claim 1, wherein a parameter of the at least two different parameters is the scleral spur depth, wherein the scleral spur depth is a distance between a point of an anterior corneal vertex and the reference frontal plane defined by the line connecting the at least two contralateral landmarks of the scleral spur.

7. The method of claim 1, wherein the at least two contralateral landmarks of the same type comprise two points of an iris pigment epithelium.

8. The method of claim 1, wherein the at least two contralateral landmarks of the same type comprise two points of a ciliary apex.

9. The method of claim 1, wherein the receiving is performed by an imaging device comprising one of: an ultrasound biomicroscope or an optical coherence tomography device.

* * * * *